US005950808A

United States Patent [19]
Tanabe et al.

[11] Patent Number: 5,950,808
[45] Date of Patent: Sep. 14, 1999

[54] ELECTROLUMINESCENT LIGHT ELEMENT, MANUFACTURING METHOD OF THE SAME, AND AN ILLUMINATED SWITCH UNIT USING THE SAME

[75] Inventors: Koji Tanabe; Masahiro Ohara; Masaru Kuwahara, all of Osaka, Japan

[73] Assignee: Matsushita Electric Industrial Co., Ltd., Osaka, Japan

[21] Appl. No.: 08/961,775

[22] Filed: Oct. 31, 1997

Related U.S. Application Data

[62] Division of application No. 08/679,091, Jul. 12, 1996, Pat. No. 5,844,362.

[30] Foreign Application Priority Data

| | | | |
|---|---|---|---|
| Jul. 14, 1995 | [JP] | Japan | 7-178490 |
| Jul. 14, 1995 | [JP] | Japan | 7-178499 |

[51] Int. Cl.[6] .......... A01H 9/18
[52] U.S. Cl. .......... 200/314; 200/512; 200/516
[58] Field of Search .......... 200/314, 512, 200/516, 5 A

[56] References Cited

U.S. PATENT DOCUMENTS

| | | | |
|---|---|---|---|
| 4,024,368 | 5/1977 | Shattuck | 200/314 |
| 4,163,883 | 8/1979 | Boulanger | 200/314 |
| 4,320,268 | 3/1982 | Brown | 200/314 X |
| 4,532,395 | 7/1985 | Zukowski | 200/314 |
| 4,551,598 | 11/1985 | Hamilton et al. . | |
| 4,665,342 | 5/1987 | Topp et al. . | |
| 4,683,359 | 7/1987 | Wojtanek | 200/314 |
| 4,708,914 | 11/1987 | Kamijo | 428/690 |
| 4,745,334 | 5/1988 | Kawachi | 313/512 |
| 5,036,249 | 7/1991 | Pike-Biegunski et al. | 313/509 |
| 5,045,656 | 9/1991 | Kojima . | |
| 5,122,626 | 6/1992 | Shinohara et al. . | |
| 5,140,116 | 8/1992 | Schmitt-Walter . | |
| 5,332,946 | 7/1994 | Eckersley et al. | 313/506 |
| 5,392,202 | 2/1995 | Herron . | |
| 5,410,217 | 4/1995 | LaPointe . | |
| 5,747,756 | 5/1998 | Boedecker | 200/5 A |

FOREIGN PATENT DOCUMENTS

| | | |
|---|---|---|
| 0357443 | 3/1990 | European Pat. Off. . |
| 0545558 | 6/1993 | European Pat. Off. . |
| 1-255118 | 10/1989 | Japan . |
| 2-148633 | 6/1990 | Japan . |
| 4-192231 | 7/1992 | Japan . |
| 8503596 | 8/1985 | WIPO . |
| 9630919 | 10/1996 | WIPO . |

OTHER PUBLICATIONS

Database WPI, Section E1, Week 8526, Derwent Publications Ltd., London, GB; Class T04, AN 85–155611, XP002042904 & JP60–086716A (Toshiba K.K.), May 16, 1985.

*Primary Examiner*—Renee S. Luebke
*Attorney, Agent, or Firm*—Pollock, Vande Sande & Amernick

[57] ABSTRACT

All of a transparent electrode layer 2, a light-emitting layer 3, a dielectric layer 4, a back-surface electrode 5, collecting electrodes 5*a*, 5*b*, and an insulating coat layer 6 are laminated with predetermined patterns by screen printing on a insulating transparent film 1. Conductive paste used for forming transparent electrode layer 2 comprises conductive powder of indium oxide which contains needle-like powder (A) and fine-grain powder (B) at a blending ratio of (A):(B)=100:0 to 20:80. A binder resin (D), being a photo-hardening or thermal-hardening resin, is mixed with the conductive powder (C) at a blending ratio of (C):(D)=45:55 to 95:5, thereby obtaining an excellent EL lighting element. In an illuminated switch unit, a switch operating projection 14 is provided on the reverse surface of an EL lighting element 15 and this EL lighting element 15 is fixed above a membrane switch 13 via a spacer 16, thereby removing any obstacles interrupting or intercepting illumination light emitted from EL lighting element 15.

10 Claims, 6 Drawing Sheets

FIG. 9
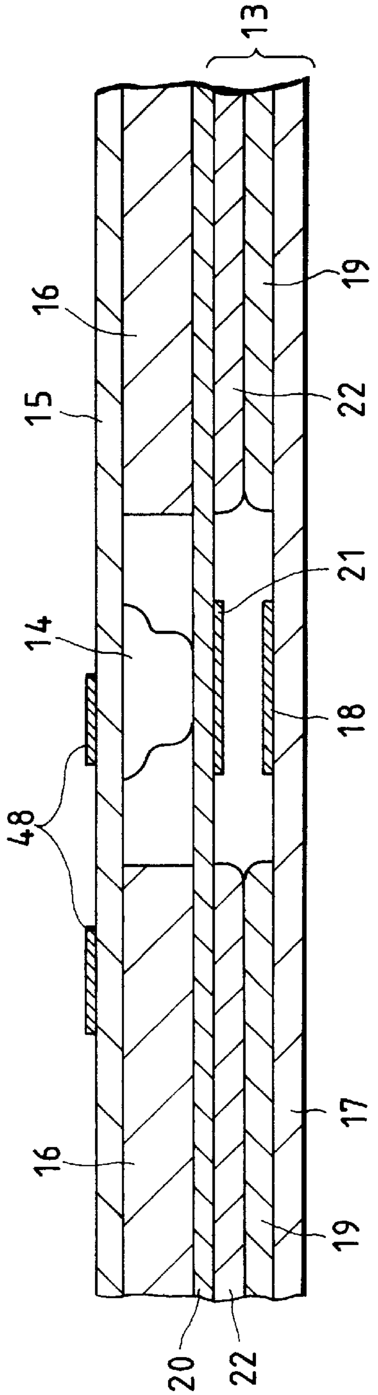
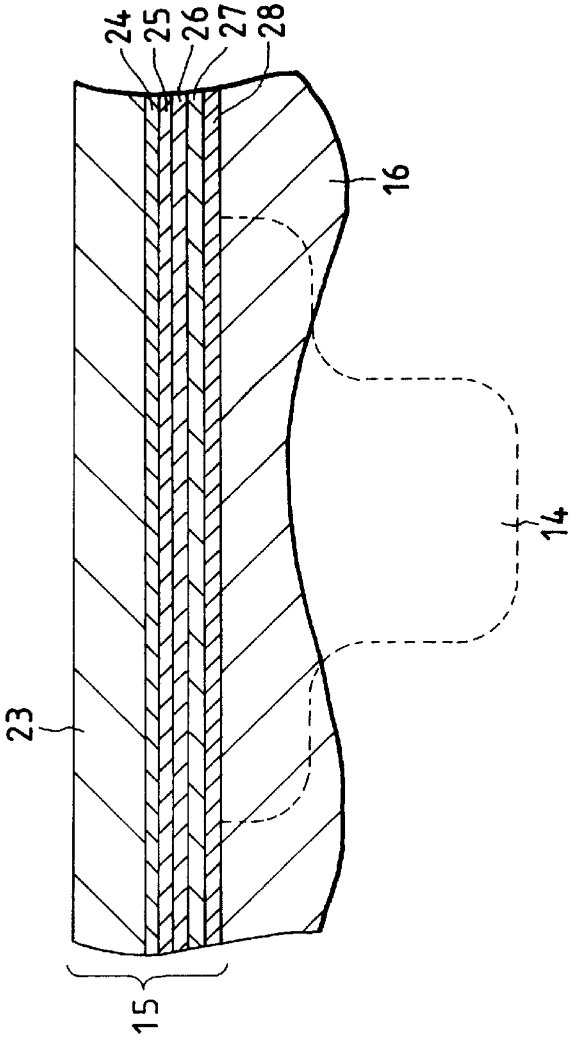
FIG. 10

ELECTROLUMINESCENT LIGHT ELEMENT, MANUFACTURING METHOD OF THE SAME, AND AN ILLUMINATED SWITCH UNIT USING THE SAME

This application is a continuation of U.S. patent application Ser. No. 08/679,091, filed Jul. 12, 1996, and now U.S. Pat. No. 5,844,362.

BACKGROUND OF THE INVENTION

1. Field of the Invention

The present invention relates to an electroluminescent (EL) lighting element preferably used for illumination of various electronic components, and a manufacturing method of the EL lighting element. Furthermore, the present invention relates to an illuminated switch unit using this EL lighting element preferably applicable to input operating sections of various electronic devices.

2. Prior Art

Recent developments of micro IC drive inverters have increased the need for an EL lighting element which is thin and capable of realizing a proper surface lighting serving as a backlight for liquid crystal display units and switches of various electronic components, such as communication devices, video devices, and acoustic devices.

FIG. 6 is a plan view showing this kind of conventional diffusion-type EL lighting element. FIG. 7 is a cross-sectional view taken along a line A-B of FIG. 6. A transparent conductive film 112 is formed on an upper surface of an insulating transparent film 101, such as polyethylene terephthalate (PET) film, by depositing stannic indium oxide on the entire surface of the insulating transparent film 101 by sputtering. A light-emitting layer 103 is pattern printed on the transparent conductive film 112 by screen printing or the like, and is then dried. Composition of light-emitting layer 103 itself is made by dissolving high-dielectric resin, such as cyanoethyl pullulan or vinylidene fluoride group rubber, in organic solvent, such as dimethyl formamide or N-methyl pidoridone, and then diffusing illuminant, such as zinc sulfide, therein. A dielectric layer 104 is formed on light-emitting layer 103. Dielectric layer 104 contains high-dielectric material, such as barium titanate, diffused in a similar resin used in light-emitting layer 103.

Furthermore, a back-surface electrode layer 105 is formed on dielectric layer 104 by using a carbon resin group paste or a silver resin group paste. An insulating coat layer 106 is formed on back-surface electrode layer 105 by using an insulating paste. These dielectric layer 104, back-surface electrode layer 105 and insulating coat layer 106 are laminated in this order by pattern printing and drying each of them successively. A collecting electrode 105*b* of transparent conductive film 112 is made by partly extending transparent conductive film 112 from the boundary of the laminated layers of light-emitting layer 103, dielectric layer 104, back-surface electrode layer 105 and insulating coat layer 106, and pattern printing a silver resin group paste etc. on thus exposed surface of transparent conductive film 112 and then drying the printed paste. Meanwhile, a collecting electrode 105*a* of back-surface electrode layer 105 is made by exposing an end region of back-surface electrode layer 105 from insulating coat layer 106.

Furthermore, in a case where a distance between collecting electrodes 105*a* and 105*b* needs to be elongated, it is possible to add an insulating film 113, such as epoxy group resin, to compensate for the poor bondability between the high-dielectric resin used in dielectric layer 104 and transparent conductive film 112, as shown in FIG. 8.

However, according to the above-described conventional arrangement, PET film on which transparent conductive film 112 is formed by sputtering is expensive. If collecting electrodes 105*a* and 105*b* of the EL lighting element are extended externally, the PET film with transparent conductive film 112 will be necessarily elongated extensively out of the light-emitting region, resulting in an increase of the cost. Furthermore, using anisotropic conductive adhesive for connecting the electrodes of such an EL lighting element to the printed circuit board is disadvantageous in that an additional insulating layer needs to be specially provided on the PET film with transparent conductive film 112 entirely formed by sputtering and, as a result, an overall thickness of the EL lighting element will be so increased that the heat conductivity is worsened and the resultant bonding is not satisfactory. Yet further, there is a possibility that a short-circuit may occur in a connection using a connector because transparent conductive film 112 is located along the entire periphery of the PET film. Hence, the connector connection will be not practically adopted. Still further, a method of removing transparent conductive film 112 in advance by etching in the region other than the light-emitting region is further expensive.

In view of the foregoing, the above-described problems can be solved by pattern printing the transparent electrode by using conductive paste having light permeability. This kind of light permeable conductive paste is already known as disclosed in Unexamined Japanese Patent Application Nos. 64-10595 and 63-10496. However, printing the light-emitting layer and the dielectric layer in a piled-up manner on the coating surface of this light permeable conductive paste will cause the following problem. Due to the presence of polar solvent, such as dimethyl formamide or N-methyl pidoridone, used for dissolving the high-dielectric resin to be involved in the light-emitting and dielectric layers, the conductivity of the EL lighting element is fairly deteriorated when high temperature is applied in the drying procedure which is mandatorily required for this kind of solvent. It means that there is a possibility that no light is emitted or very poor light emission is obtained only in the limited region near the collecting electrodes. Hence, it is not possible to print the light-emitting layer and the dielectric layer in the piled-up manner on the coating surface of this light permeable conductive paste, although it is possible to use this for back-surface electrode layer 105 or to form the transparent electrode layer and light-emitting layer 103 independently and later connect them by the laminate or the like.

Hereinafter, a conventional illuminated switch unit using such an electroluminescent lighting element will be explained.

As shown in FIG. 14, an upper insulating sheet 201 made of resin film has a reverse surface on which a movable contact 202 is printed. A lower insulating sheet 203 has an upper surface on which a stationary contact 204 is printed. Spacer 205, which is resin film having both surfaces applied with adhesive, are interposed between upper insulating sheet 201 and lower insulating sheet 203 so that movable contact 202 and stationary contact 204 are disposed in a confronting relationship with a predetermined gap therebetween when these sheets 201 and 203 are fixed to each other to form a membrane switch 206.

An electroluminescent lighting element (abbreviated as EL lighting element) 207 is disposed on this membrane switch 206. A top sheet 211, made of transparent resin film, is disposed and fixed on this EL lighting element 207 via spacer 212 of transparent resin film having adhesive applied on both surfaces thereof. Top sheet 211 has an upper surface provided with printed pattern representing letters, figures or others 208 and a lower surface provided with a button 209 which is a transparent or semi-transparent resin product bonded by adhesive 210 to the lower surface of top sheet 211, thereby constituting the conventional illuminated switch unit.

Next, an operation of the above-described conventional illuminated switch unit will be explained. Depressing top sheet 211 causes button 209 to move downward and press or push EL lighting element 207. Hence, a region of upper insulating sheet 201 which received a depressing force through EL lighting element 207 is recessed. Movable contact 202, which constitutes part of membrane switch 206 and is provided at the lower surface of the recessed portion of upper insulating sheet 201, is depressed downward. Hence, movable contact 202 can be brought into contact with stationary contact 204 provided on lower insulating sheet 203, thereby establishing an electrical connection therebetween.

However, according to the above-described conventional arrangement, the presence of button 209 and spacer 212 causes undesirable illumination such as a silhouette of these parts or irregularities of luminance. Furthermore, the manufacturing costs will be increased due to numerous parts and increased assembling processes.

SUMMARY OF THE INVENTION

Accordingly, in view of above-described problems encountered in the prior art, an object of the present invention is to provide a novel and excellent electroluminescent (EL) lighting element which is simple in construction, easy to manufacture, and stable in performances, and also provide a manufacturing method of the same. Furthermore, the present invention has as an object to provide an illuminated switch unit capable of assuring uniformity of illumination light emitted from the EL lighting element, simple in construction, and cheap in manufacturing costs.

In order to solve the above-described problems, the present invention laminates the transparent electrode layer, light-emitting layer, dielectric layer, back-surface electrode layer, collecting electrodes and insulating coat layer on the insulating transparent film successively in predetermined patterns respectively by screen printing.

More specifically, a first aspect of the present invention provides an electroluminescent lighting element comprising: an insulating transparent film serving as a base material integrally formed with an external connecting terminal; a transparent electrode layer of a predetermined pattern printed on a surface of the insulating transparent film in a region other than the external connecting terminal; a light-emitting layer of a predetermined pattern printed on the transparent electrode layer; a dielectric layer of a predetermined pattern printed on the light-emitting layer; a back-surface electrode layer of a predetermined pattern printed on the dielectric layer; a first collecting electrode printed in a predetermined pattern having one end connected to the back-surface electrode layer and the other end constituting part of the external connecting terminal of the insulating transparent film; a second collecting electrode printed in a predetermined pattern having one end connected to the transparent electrode layer and the other end constituting part of the external connecting terminal of the insulating transparent film; and an insulating coat layer printed in a predetermined pattern so as to cover a surface of the electroluminescent lighting element except for the external connecting terminal.

According to features of preferred embodiments of the present invention, the transparent electrode layer is formed by using a paste including conductive powder having light permeability which is diffused in an insulating resin or in a solution containing insulating resin. Preferably, the conductive powder is indium oxide powder, and the insulating resin is photo-hardening or thermal-hardening resin.

The indium oxide powder serving as the conductive powder comprises needle-like powder (A) and fine-grain powder (B) blended at a weight ratio (A):(B) somewhere in a range of 100:0 to 20:80, and all the conductive powder (C) is blended with the insulating resin (D) at a weight ratio (C):(D) somewhere in a range of 45:55 to 95:5.

The insulating resin diffusing the light-permeable conductive powder therein is acrylate group photo-hardening resin, or thermal-hardening resin containing at least one selected from the group consisting of epoxy resin, urethane modified epoxy resin, epoxy modified polyester resin.

It is preferable that an anisotropic conductive adhesive is applied on the first and second collecting electrodes of a distal end of the external connecting terminal and the insulating transparent film.

It is also preferable that a reinforcement board is provided on a reverse surface of the insulating transparent film in a region of the other ends of the first and second collecting electrodes constituting the external connecting terminal.

A second aspect of the present invention provides a method for manufacturing an electroluminescent lighting element, comprising the steps of: applying a light permeable paste in a predetermined pattern by screen printing on an insulating transparent film serving as a base material, and then forming a transparent electrode layer by performing a photo-hardening or thermal-hardening operation; applying a light-emitting paste in a predetermined pattern by screen printing on the transparent electrode layer, and then forming a light-emitting layer on the transparent electrode layer by performing a heating and drying operation; applying a dielectric paste in a predetermined pattern by screen printing on the light-emitting layer, and then forming a dielectric layer on the light-emitting layer by performing a heating and drying operation; applying a conductive paste in a predetermined pattern by screen printing on the dielectric layer, and then forming a back-surface electrode layer on the dielectric layer by performing a heating and drying operation; applying a conductive paste in a first pattern by screen printing in such a manner that one end of the first pattern is connected to the transparent electrode layer and the other end of the first pattern constitutes part of an external connecting terminal, and also applying a conductive paste in a second pattern by screen printing in such a manner that one end of the second pattern is connected to the back-surface electrode layer and the other end of the second pattern constitutes part of the external connecting terminal, and then forming first and second collecting electrodes by performing a heating and drying operation; and applying an insulating paste by screen printing on an entire surface of the electroluminescent lighting element except for a distal end of the external connecting terminal, and then forming an insulating coat layer by performing a heating and drying operation.

In this manufacturing method, it is preferable that the back-surface electrode layer and the collecting electrodes are integrally formed in a predetermined pattern. The collecting electrodes are formed before the transparent electrode layer is formed.

With this arrangement, the conductivity of the printing type transparent electrode layer can be maintained stably without causing an undesirable deterioration even when the lamination printing of the light-emitting layer and the dielectric layer is applied thereon. Hence, the obtainable luminance is comparable with that of the conventional EL lighting element using a transparent conductive film formed by sputtering. Furthermore, the conductivity is stable even if it is left in a high-temperature and high-humidity atmosphere, thereby assuring the reliability of EL lighting element under various environments.

Furthermore, forming all the layers including the transparent electrode layer by pattern printing in a lamination fashion is advantageous in unifying the production facilities. Even if the external connection terminal of collecting electrodes is spaced far from the light-emitting section, the only thing necessary to do is extensively forming the wiring of the collecting electrodes on the same insulating transparent film. Accordingly, the manufacturing cost for each EL lighting element is cheap.

Still further, in the case where the collecting electrodes are connected to an external device, the EL lighting element of the present invention provides neither a transparent conductive film nor an insulating film on the insulating transparent film at the region corresponding to the connecting portion, whereas the conventional EL lighting element requires these transparent conductive film and insulating film formed by sputtering entirely on the insulating transparent film. Hence, it becomes possible to apply anisotropic conductive adhesive in advance on the collecting electrodes at the distal end of the external connection terminal and also on the insulating transparent film, for realizing an easy connection of the EL lighting element with a printed circuit board. Moreover, providing the reinforcement board on the reverse surface of the insulating transparent film in the region corresponding to the distal end of the external connection terminal makes it easy to realize a connector connection.

In order to solve the above-described problems, the present invention further provides an illuminated switch unit comprising an EL lighting element having a reverse surface provided with a switch operating projection which constitutes an operating means to be disposed above a push switch.

More specifically, a third aspect of the present invention provides an illuminated switch unit comprising: a push switch having a movable contact and a stationary contact disposed in a confronting relationship with a predetermined gap; and an electroluminescent lighting element provided above the push switch, the electroluminescent lighting element having a reverse surface provided with a push-switch operating projection for depressing the movable contact to turn on the push switch.

In the above illuminated switch unit, it is preferable that the push-switch operating projection is formed by printing insulating resin. Alternatively, the push-switch operating projection is formed by bonding a rigid member. It is further preferable that the electroluminescent lighting element is a diffusion-type electroluminescent lighting element. Furthermore, it is preferable that a surface of the electroluminescent lighting element, serving as a light-emitting surface, is provided with printed pattern representing letters, figures or others. Yet further, the push switch is a membrane switch with or without click motion. The push switch is a push switch with click motion, and the movable contact is a metallic thin plate configured in a diaphragm shape.

With this arrangement, it becomes possible to remove any obstacles interrupting or intercepting illumination light emitted from the EL lighting element. Hence, uniformity of illumination light emitted from the EL lighting element can be surely attained. Furthermore, the construction becomes simple, and the manufacturing costs can be reduced largely.

BRIEF DESCRIPTION OF THE DRAWINGS

The above and other objects, features and advantages of the present invention will become more apparent from the following detailed description which is to be read in conjunction with the accompanying drawings, in which:

FIG. 9 is a cross-sectional view showing an arrangement of an illuminated switch unit in accordance with a seventh embodiment of the present invention.

FIG. 10 is a cross-sectional view showing details of an EL lighting element of the seventh embodiment of the present invention;

DETAILED DESCRIPTION OF THE PREFERRED EMBODIMENTS

Figure 1:
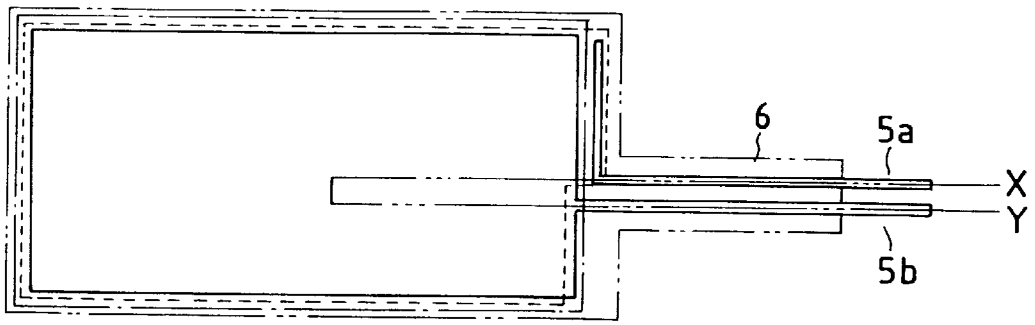
FIG. 1 is a plan view showing an EL lighting element in accordance with a first embodiment of the present invention.

Hereinafter, preferred embodiments of the present invention will be explained with reference to the accompanying drawing.

First Embodiment

Hereinafter, a first embodiment of the present invention will be explained with reference to FIGS. 1 and 2.

An insulating transparent film 1 is a polyethylene terephthalate (abbreviated as PET, hereinafter) film of 75 $\mu$m. A transparent electrode layer 2 having a dry film thickness of 3 to 5 $\mu$m is pattern printed on this insulating transparent film 1 by screen printing a transparent electrode paste. This transparent electrode paste is produced by the following procedure. First, thermal-hardening insulating resin (which is formed by mixing epoxy resin #828 commercially available from Yuka Shell Co., Ltd. and phenoxy resin YP-40 commercially available from Touto Kasei Co., Ltd. at the same weight ratio and then adding imidazole block isocyanate G8009B commercially available from Daiichi Kogyo Seiyaku Co., Ltd. as hardening agent at 1.5 weight part per 100 weight part of the above mixture) is mixed with indium oxide powder (SCP-X of Sumitomo Metal Mining Co., Ltd.) of 60 weight % and then is subjected to a three-roll diffusing operation. Subsequently, solvent (isophorone) is appropriately added to adjust the viscosity of the transparent electrode paste at 13 Pa. The transparent electrode paste, thus screen printed, is dried at 155° C. for 15 minutes, thereby pattern forming the transparent electrode layer 2 having the dry film thickness of 3 to 5 μm.

In the same manner, the following pastes are successively accumulated on the transparent electrode layer 2 at predetermined patterns to form a multi-layer construction of light-emitting layer 3, dielectric layer 4, back-surface electrode layer 5, and insulating coat layer 6.

Light-emitting layer 3: a paste forming the light-emitting layer 3 is produced by the following procedure. A mixed solution of 50 g, consisting of cyanoethyl pullulan resin of 70 weight % and cyanoethyl polyvinyl alcohol resin of 30 weight % (i.e. a solution obtained by dissolving CR-M of 30 weight % with formamide; CR-M is a product commercially available from Shinetsu Chemical Co., Ltd.) is mixed with imidazole block isocyanate (G 8009B supplied by Daiichi Kogyo Seiyaku Co., Ltd.) of 2 g serving as hardening agent. Then, illuminant (TYPE 40 of Sylvania Corporation) of 100 g is added to thus obtained mixture and is stirred and diffused therein. A dry thickness of resultant light-emitting layer 3 was 35 μm.

Dielectric layer 4: a paste forming the dielectric layer 4 is produced by the following procedure. That is, vinylidene fluoride copolymer rubber solution of 53 g (a solution obtained by dissolving DAIEL G902 of 35 weight % with isophorone; Daiel G902 is a commercially available product from Daikin Industry Co., Ltd.) is mixed with the hardening agent consisting of 0.02 g Di-cumyl peroxide and 50 g $BaTiO_3$ powder (commercially available from Kantou Chemical Co., Ltd.) by performing the three-roll diffusing operation. Thus formed paste had a dry film thickness of 35 μm.

Back-surface electrode layer 5: a paste forming the back-surface electrode layer 5 is a conductive paste (DW-250H of Toyobo Co., Ltd.) A resultant film had a dry thickness of 10 μm.

Insulating coat layer 6: a paste forming the insulating coat layer 6 is an insulating paste (XB-804A of Fujikura Kasei Co., Ltd.). A resultant film had a dry film thickness of 30 μm.

Figure 2:
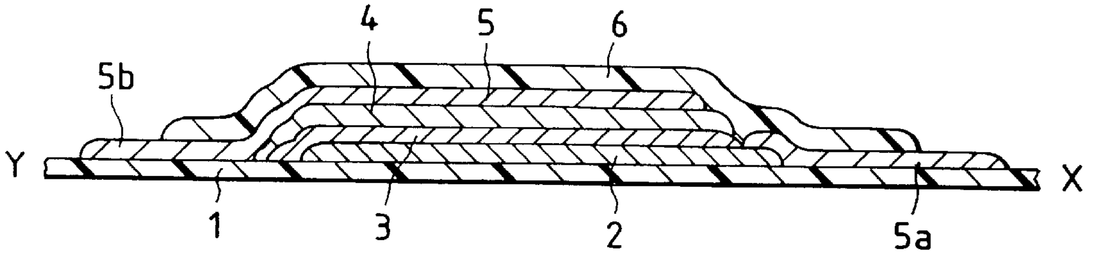
FIG. 2 is a cross-sectional view taken along a line X-Y of FIG. 1.

FIG. 1 shows a plan view showing the EL lighting element produced by performing the above-described lamination printing method. FIG. 2 is a cross-sectional view taken along a line X-Y of FIG. 1. In this embodiment, collecting electrodes 5*a* and 5*b*are integrally formed with the back-surface electrode layer 5 by performing a simultaneous pattern printing operation. When electric voltage 100 V of 400 Hz was applied on these collecting electrodes 5*a* and 5*b*, an initial luminance of 74.8 $Cd/m^2$ was obtained. Then, the 50% luminance decline period was measured by leaving the light-emitting sample of this embodiment in a tank of 70° C. and a tank of 40° C./90–95% RH. As a result, the 50% luminance decline period was 300 hours in the 70° C. tank, and was the 1,000 hours in the 40° C./90–95% RH tank.

The indium oxide powder serving as the conductive powder comprises needle-like powder (A) and fine-grain powder (B) blended at a predetermined weight ratio (A):(B). When the ratio of needle-like powder (A) is less than 20%, the conductivity is largely deteriorated in the lamination printing process of light-emitting layer 3 and dielectric layer 4 and also in the succeeding drying process. Hence, the luminance is lowered correspondingly. When this sample is left in an atmosphere of high temperature and high humidity, the luminance is further worsened. Furthermore, when the ratio of all the conductive powder (C) to the insulating resin (D) is not larger than 45%, the conductivity is so declined that no light can be obtained from the EL lighting element and the dispersion of the luminance is enlarged. On the other hand, when the ratio of all the conductive powder (C) to the insulating resin (D) is not less than 95%, it becomes impossible to obtain a uniform film layer in the printing operation. Hence, the light permeability is deteriorated. The luminance will be also deteriorated, and the dispersion of the luminance will be enlarged. In view of the balance between the light permeability and the conductivity and also the stability of the conductivity under the lamination printing operation and possible environmental changes, the following desirable ratios are defined based an the experimental data.

(A):(B)=100:0 through 40:60

(C):(D)=55:45 through 80:20

Furthermore, it was confirmed that a similar result could be obtained by printing collecting electrodes 5*a* and 5*b* in advance before forming transparent electrode layer 2.

Second-Embodiment

The thermal-hardening insulating resin contained in the transparent electrode paste, used in the first embodiment, was set to the same solid-state ratio. And, in the same manner as the first embodiment, several EL lighting elements were experimentally fabricated by using various transparent electrode pastes including the following resins.

a) Photo-hardening resin: acrylate group resin (3031 of Three Bond Corporation);

b) Photo-hardening resin: acrylate group resin (UR 3000 of Mitsubishi Rayon Co., Ltd.);

c) Thermal-hardening resin: urethane modified epoxy resin of 70 weight % (EPU-6A of Asahi Denka Kogyo K.K.) is mixed with polyester resin of 30weight % (#300 of Toyobo Co., Ltd). And then, imidazole block isocyanate (G8009B of Daiichi Kogyo Seiyaku Co., Ltd.) serving as hardening agent is added with the resultant mixture at 20 weight part per 100 weight part of the resin;

d) Thermal-hardening resin: epoxy resin of 60 weight % (#828 of Yuka Shell Co., Ltd.) is mixed with epoxy modified polyester resin of 40 weight % (EP2940 of Toyobo Co., Ltd). And then, imidazole block isocyanate (G8009B of Daiichi Kogyo Seiyaku Co., Ltd.) serving as hardening agent is added with the resultant mixture at 10 weight part per 100 weight part of the resin;

e) Comparative example: 5 weight part of oxime block isocyanate (KE1001 of Daiichi Kogyo Seiyaku Co., Ltd.) serving as hardening agent is added to 100 weight part of cyanoethyl resin (CR-M of Shin-etsu Chemical Co., Ltd.);

f) Comparative example: 3 weight part of melamine serving as hardening agent is added to 100 weight part of polyvinylidene fluoride group rubber (Daiel G201 of Daikin Industry Co., Ltd.); and g) Comparative example: urethane modified polyester resin (UR8300 of Toyobo Co., Ltd.).

In the case of the photo-hardening resin of sample a), its film was hardened by using a UV lamp having its light-emitting wavelength of 300 to 400 nm. When electric voltage 100 V of 400 Hz is applied, a resultant initial luminance was 76.2 $Cd/m^2$ for sample a), 70.3 $Cd/m^2$ for sample b), 74.6 $Cd/m^2$ for sample c), and 75.6 $Cd/m^2$ for sample d). Regarding the luminance decline during the continuous lighting in the atmosphere of 70° C. and 60° C./90–95%RH, resultant data were substantially identical with those of the first embodiment.

Two comparative examples e) and g) caused no light emission. Another comparative example f) caused a small amount of light emission in the vicinity of collecting electrode 5*a*.

Third Embodiment

The conductive power of the transparent electrode paste, used in this embodiment, was a mixture of needle-like stannic indium oxide (SCP-SX of Sumitomo Metal Mining Co., Ltd.) and fine-grain stannic indium oxide (UFP-X of Sumitomo Metal Mining Co., Ltd.). And, its blending ratio was changed variously. Furthermore, the blending ratio of all the conductive powder to the insulating resin was also changed. Numerous EL lighting elements were fabricated by combining these two parameters in a matrix. Then, luminance value, irregularities of luminance, and resistance value of the transparent electrode of each finished product of the fabricated EL lighting element were measured.

Table 1 shows the result of the measurements.

expressed in terms of kΩ. When each of the above-described samples includes needle-like conductive powder not larger than 10%, its luminance value was greatly lowered or reduced to zero by leaving this sample in the atmosphere of 40° C./90–95%RH.

Fourth Embodiment

Figure 3:
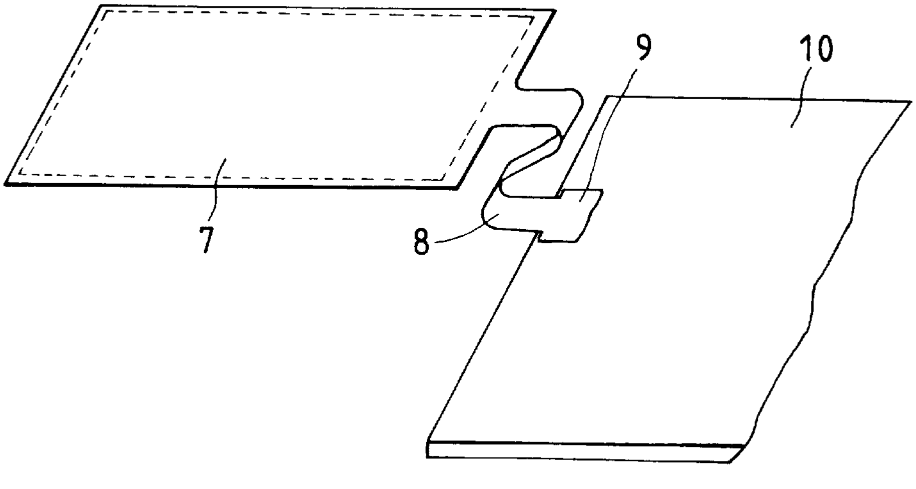
FIG. 3 is a perspective view showing an EL lighting element and a printed circuit board connected by anisotropic conductive adhesive in accordance with the fourth embodiment of the present invention.

A thermocompression bonding terminal 9, provided at the distal end of collecting electrodes 5*a* and 5*b* of the EL lighting element of the first embodiment, was connected to a printed circuit board 10 by using anisotropic conductive adhesive (CP7131 of Sony Chemical Co., Ltd.) under thermocompression bonding conditions of 180° C., 35 kg/cm$^2$ and 30 sec. FIG. 3 shows a connected condition of thermocompression bonding terminal 9 and printed circuit board 10. A driving inverter circuit is mounted on printed circuit board 10 to activate or turn on a light-emitting section 7. The light-emitting condition was not at all changed by bending a wiring harness 8 of the collecting electrodes in any way.

Fifth Embodiment

A reinforcement board 11, which is PET film of 188 μm with adhesive on its surface is bonded on the reverse surface of collecting electrodes 5*a* and 5*b* of the EL lighting element

TABLE 1

| | wt % | | | | | | | | | |
|---|---|---|---|---|---|---|---|---|---|---|
| | 0 | 10 | 20 | 30 | 40 | 50 | 60 | 70 | 80 | 100 |
| 30% | | | | | | | | | | |
| kΩ | ∞ | ∞ | ∞ | ∞ | ∞ | ∞ | ∞ | ∞ | ∞ | ∞ |
| Cd/m$^2$ | 0 | 0 | 0 | 0 | 0 | 0 | 0 | 0 | 0 | 0 |
| 40% | | | | | | | | | | |
| kΩ | ∞ | ∞ | ∞ | ∞ | ∞ | ∞ | ∞ | ∞ | ∞ | 14 |
| Cd/m$^2$ | 0 | 0 | 0 | 0 | 0 | 0 | 0 | 0 | 0 | 69 |
| 50% | | | | | | | | | | |
| kΩ | ∞ | ∞ | ∞ | ∞ | ∞ | ∞ | ∞ | ∞ | 12 | .76 |
| Cd/m$^2$ | 0 | 0 | 0 | 0 | 0 | 0 | 0 | 0 | 72 | 75 |
| 60% | | | | | | | | | | |
| kΩ | ∞ | ∞ | ∞ | ∞ | ∞ | ∞ | 3000 | 4.8 | .54 | .15 |
| Cd/m$^2$ | 0 | 0 | 0 | 0 | 0 | 0 | 21 | 74 | 75 | 74 |
| 70% | | | | | | | | | | |
| kΩ | ∞ | ∞ | ∞ | 860 | 25 | 8.5 | 2.1 | .52 | .22 | .12 |
| Cd/m$^2$ | 0 | 0 | 0 | 36 | 66 | 69 | 73 | 73 | 71 | 68 |
| 80% | | | | | | | | | | |
| kΩ | 3500 | 4700 | 210 | 10 | 4.6 | 1.5 | .41 | .18 | .12 | .11 |
| Cd/m$^2$ | 13 | 12 | 51 | 72 | 74 | 72 | 69 | 69 | 67 | 63 |
| 90% | | | | | | | | | | |
| kΩ | 250 | 125 | 6.8 | 1.8 | .32 | .18 | .14 | .12 | .11 | — |
| Cd/m$^2$ | 48 | 49 | 55 | 68 | 69 | 66 | 66 | 66 | 65 | — |
| 95% | | | | | | | | | | |
| kΩ | ∞ | ∞ | ∞ | 126 | 75 | — | — | — | — | — |
| Cd/m$^2$ | 0 | 0 | 0 | 56 | 57 | — | — | — | — | — |
| 96% | | | | | | | | | | |
| kΩ | ∞ | ∞ | ∞ | 220 | — | — | — | — | — | — |
| Cd/m$^2$ | 0 | 0 | 0 | 23 | — | — | — | — | — | — |

Figure 4:
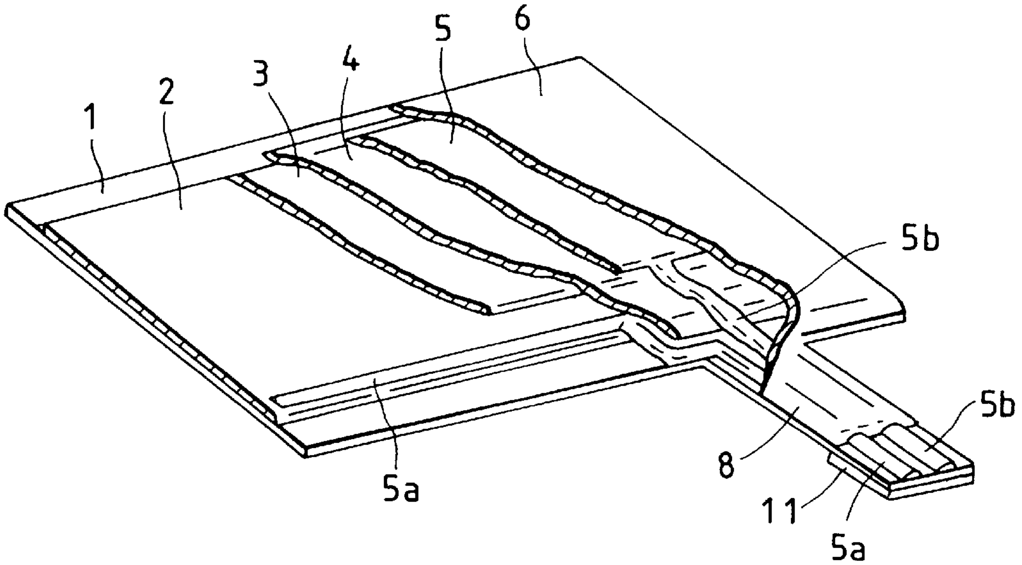
FIG. 4 is a partly cross-sectional perspective view showing the arrangement of layers constituting an EL lighting element enabling the connector connection in accordance with a fifth embodiment of the present invention.

In table 1, 0 to 100 wt % represents the ratio of the needle-like powder to all the conductive powder, while 30 to 96 % represents the blending ratio of all the conductive powder to the insulating resin. Infinity (∞) represents a resistance value larger than 10 MΩ, and "–" represents the experimental result that no paste was obtained and therefore no printing operation was performed. The luminance value is expressed in terms of Cd/m$^2$, and the resistance value is of the first embodiment, to fabricate an EL lighting element capable of connecting a film connector. FIG. 4 is a partly cross-sectional view showing each layer of the fifth embodiment EL lighting element.

Sixth Embodiment

The arrangement of collecting electrodes 5*a* and 5*b*, back-surface electrode layer 5 and insulating coat layer 6 are modified in the following manner.

Collecting electrodes 5*a* and 5*b*: conductive paste (DW-250H of Toyobo Co., Ltd.) having a dry film thickness of 10 $\mu$m.

Back-surface electrode layer 5: conductive paste (DY-150H of Toyobo Co., Ltd.) having a dry film thickness of 8 $\mu$m.

Insulating coat layer 6: insulating paste (TSE3221 of Toshiba Silicon Co., Ltd.) having a dry film thickness of 25 $\mu$m.

Figure 5:
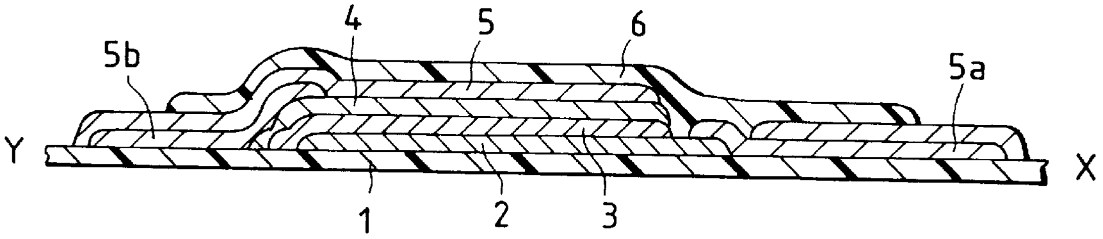
FIG. 5 is a cross-sectional view similar to FIG. 2 but showing an arrangement of an EL lighting element in accordance with a sixth embodiment of the present invention.
Figure 6:
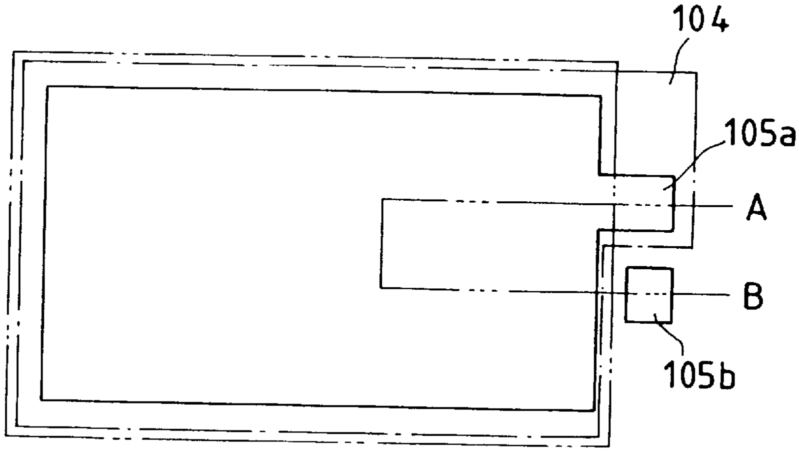
FIG. 6 PRIOR ART
FIG. 6 is a plan view showing a conventional EL lighting element.
Figure 7:
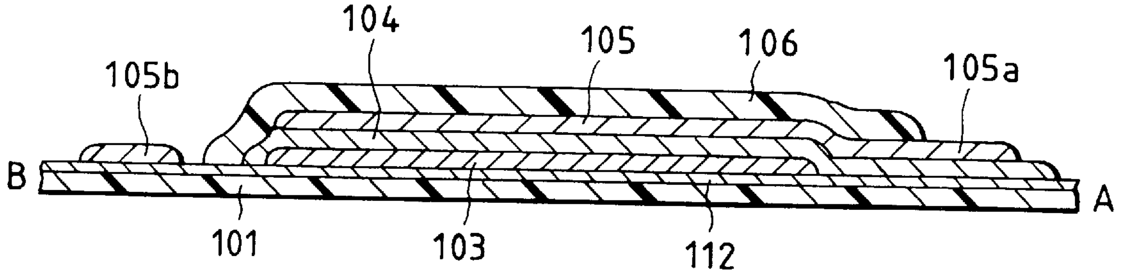
FIG. 7 PRIOR ART
FIG. 7 is a cross-sectional view taken along a line A-B of FIG. 6.
Figure 8:
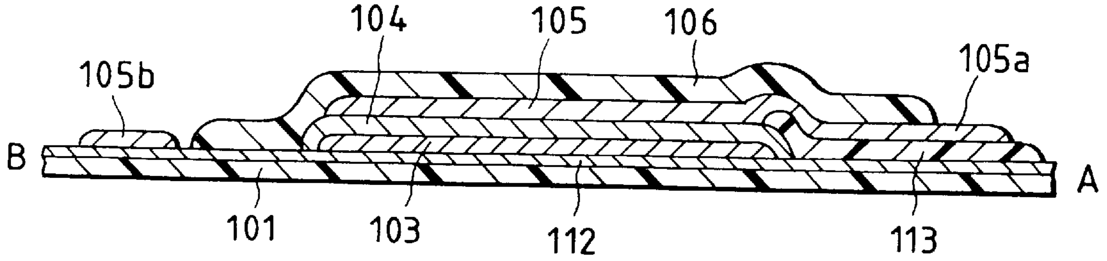
FIG. 8 PRIOR ART
FIG. 8 is a cross-sectional view similar to FIG. 7 but showing another conventional EL lighting element.

By performing the lamination printing operation of these layers, an EL lighting element having a cross section shown in FIG. 5 is fabricated. Collecting electrodes 5*a* and 5*b* is made from a silver resin group paste, while back-surface electrode layer 5 is made from a carbon resin group paste.

When electric voltage 100 V of 400 Hz was applied to the EL lighting element of the sixth embodiment, a resultant initial luminance was 72.3 Cd/cm$^2$.

As explained in the foregoing description of the first to sixth embodiments, the EL lighting element of the present invention does not cause a deterioration of the conductivity of the transparent electrode layer even if the light-emitting layer and the dielectric layer are pattern printed in the piled-up manner on the transparent electrode layer. In other words, all of the layers including the transparent electrode layer can be formed by (screen) printing. Hence, the production cost is cheap and electrical connection of the collecting electrodes can be easily done.

Furthermore, a flexible printed circuit board (FPC) is generally known as having a circuit wiring pattern printed by conductive paste on an insulating transparent film such as PET. The present invention makes it possible to form an EL lighting element at a desired portion on the FPC by pattern printing, bringing large merits in various industries.

As apparent from the foregoing description, the present invention provides an electroluminescent lighting element comprising: an insulating transparent film (1) serving as a base material integrally formed with an external connecting terminal (8); a transparent electrode layer (2) of a predetermined pattern printed on a surface of the insulating transparent film in a region other than the external connecting terminal; a light-emitting layer (3) of a predetermined pattern printed on the transparent electrode layer; a dielectric layer (4) of a predetermined pattern printed on the light-emitting layer; a back-surface electrode layer (5) of a predetermined pattern printed on the dielectric layer; a first collecting electrode (5*b*) printed in a predetermined pattern having one end connected to the back-surface electrode layer and the other end constituting part of the external connecting terminal of the insulating transparent film; a second collecting electrode (5*b*) printed in a predetermined pattern having one end connected to the transparent electrode layer and the other end constituting part of the external connecting terminal of the insulating transparent film; and an insulating coat layer (6) printed in a predetermined pattern so as to cover a surface of the electroluminescent lighting element except for the external connecting terminal.

According to features of preferred embodiments of the present invention, the transparent electrode layer (2) is formed by using a paste including conductive powder having light permeability which is diffused in an insulating resin or in a solution containing insulating resin. Preferably, the conductive powder is (stannic) indium oxide powder, and the insulating resin is photo-hardening or thermal-hardening resin.

The indium oxide powder serving as the conductive powder comprises needle-like powder (A) and fine-grain powder (B) blended at a weight ratio (A):(B) somewhere in a range of 100:0 to 20:80, and all the conductive powder (C) is blended with the insulating resin (D) at a weight ratio (C):(D) somewhere in a range of 45:55 to 95:5.

The insulating resin diffusing the light-permeable conductive powder therein is acrylate group photo-hardening resin, or thermal-hardening resin containing at least one selected from the group consisting of epoxy resin, urethane modified epoxy resin, epoxy modified polyester resin.

It is preferable that an anisotropic conductive adhesive is applied on the first and second collecting electrodes of a distal end of the external connecting terminal and the insulating transparent film.

It is also preferable that a reinforcement board is provided on a reverse surface of the insulating transparent film in a region of the other ends of the first and second collecting electrodes constituting the external connecting terminal.

Still further, the present invention provides a method for manufacturing an electroluminescent lighting element, comprising the steps of: applying a light permeable paste in a predetermined pattern by screen printing on an insulating transparent film (1) serving as a base material, and then forming a transparent electrode layer (2) by performing a photo-hardening or thermal-hardening operation; applying a light-emitting paste in a predetermined pattern by screen printing on the transparent electrode layer, and then forming a light-emitting layer (3) on the transparent electrode layer by performing a heating and drying operation. A dielectric paste is applied in a predetermined pattern by screen printing on the light-emitting layer, and then a dielectric layer (4) is formed on the light-emitting layer by performing a heating and drying operation. A conductive paste is applied in a predetermined pattern by screen printing on the dielectric layer, and then a back-surface electrode layer (5) is formed on the dielectric layer by performing a heating and drying operation. A conductive paste in a first pattern is applied by screen printing in such a manner that one end of the first pattern is connected to the transparent electrode layer and the other end of the first pattern constitutes part of an external connecting terminal. Also applying a conductive paste is applied in a second pattern by screen printing in such a manner that one end of the second pattern is connected to the back-surface electrode layer and the other end of the second pattern constitutes part of the external connecting terminal. First and second collecting electrodes (5*a*, 5*b*) are formed by performing a heating and drying operation. An applying an insulating paste is then applied by screen printing on an entire surface of the electroluminescent lighting element except for a distal end of the external connecting terminal, and then forming an insulating coat layer (6) by performing a heating and drying operation.

In this manufacturing method, it is preferable that the back-surface electrode layer (5) and the collecting electrodes (5*a*, 5*b*) are integrally formed in a predetermined pattern. The collecting electrodes are formed before the transparent electrode layer is formed.

Seventh Embodiment

Hereinafter, a seventh embodiment of the present invention relating to an illuminated switch unit using the electroluminescent lighting element described in the above first through sixth embodiments will be explained with reference to the accompanying drawings.

As shown in FIG. 9, an EL lighting element 15 having a reverse surface provided with a switch operating projection 14 is disposed on a membrane switch 13 via spacer 16 which is an adhesive sheet made of resin film having a thickness of approximately 200 $\mu$m and having on both surfaces applied adhesive.

An arrangement of membrane switch 13 will be explained in more detail, hereinafter. A lower insulating sheet 17, made of resin film having a thickness of approximately 100 μm, has an upper surface on which a lower stationary contact 18 is formed by printing using a silver resin group or carbon resin group paste. Then, a lower insulating spacer 19 is formed on the lower insulating sheet 17 so as to cover a region other than this lower stationary contact 18 by using semi-transparent vinyl acetate=vinyl chloride group insulating paste, thereby exposing this lower stationary contact 18. An upper movable contact 21 is printed on a reverse (lower) surface of an upper insulating sheet 20, made of resin film having a thickness of approximately 100 μm, by using a silver resin group or carbon resin group paste, in such a manner that upper movable contact 21 is disposed in a confronting relationship with lower stationary contact 18. An upper insulating spacer 22 is formed around this upper movable contact 21 using semi-transparent insulating paste so as to expose this movable contact 21. Thus, when lower insulating sheet 17 and upper insulating sheet 20 are disposed in position, lower stationary contact 18 and upper movable contact 21 are brought into a confronting relationship with a predetermined gap therebetween. Lower insulating spacer 19 and upper insulating spacer 22 are fixed with each other by applying pressure and heat.

Next, EL lighting element 15 will be explained in more detail with reference to FIG. 10. A base sheet 23, made of insulating transparent film having a thickness of 100 μm, has a reverse (lower) surface on which a transparent electrode layer 24 is printed by using a transparent electrode paste. This transparent electrode paste contains indium oxide power added and diffused into insulating resin. A light-emitting layer 25 is printed on a lower surface of this transparent electrode layer 24 by using a paste containing zinc sulfide phosphor powder stirred and diffused into binder resin. A dielectric layer 26 is printed on a lower surface of this light-emitting layer 25 by using a paste containing barium titanate powder stirred and diffused into binder resin. Still further, a back-surface electrode layer 27 is printed on a lower surface of this dielectric layer 26 by using a carbon resin group paste. Finally, an insulating coat layer 28 is printed on a lower surface of this back-surface electrode layer 27 by using an insulating paste.

A switch operating projection 14 is printed by using an epoxy group resin at a predetermined position on a lower surface of insulating coat layer 28, so that this switch operating projection 14 can be positioned concentrically with lower stationary contact 18 and upper movable contact 21 of membrane switch 13 when EL lighting element 15 is placed on membrane switch 13 by keeping back-surface electrode layer 28 at bottom.

Provided on an upper surface of EL lighting element 15 are printed patterns 48 representing letters, figures or other indicia.

Next, an operation of the above-described illuminated switch unit of the present embodiment will be explained. When EL lighting element 15 is depressed downward, switch operating projection 14 moves downward and pushes upper movable contact 21 of membrane switch 13 so that upper movable contact 21 can be brought into contact and electrically connected with lower stationary contact 18 of membrane switch 13.

With the above-described arrangement, it becomes possible to remove any obstacles interrupting or intercepting illumination light emitted from EL lighting element 15. Hence, uniformity of illumination light emitted from EL lighting element 15 can be surely obtained. Furthermore, the construction of the illuminated switch unit becomes simple and suitable for mass-production and, hence, the manufacturing costs of the same can be reduced largely.

Eighth Embodiment

Hereinafter, an eighth embodiment of the present will be explained.

Figure 11:
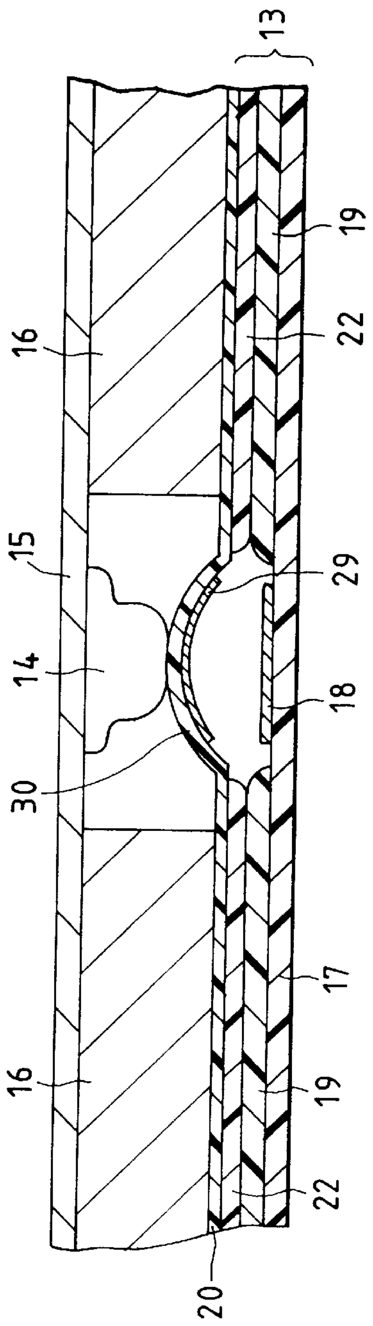
FIG. 11 is a cross-sectional view showing an arrangement of an illuminated switch unit in accordance with an eighth embodiment of the present invention.

As shown in FIG. 11, the eighth embodiment is different from the seventh embodiment in that a movable contact 29 is provided on a lower surface of a diaphragm 30 configured or squeezed into a dome shape by thermally molding upper insulating sheet 20 of membrane switch 13.

With this arrangement, it becomes possible to obtain a crisp and better click feeling in the operation of the switch, in addition to the effects obtained from the above-described seventh embodiment.

Ninth Embodiment

Hereinafter, a ninth embodiment of the present invention will be explained.

Figure 12:
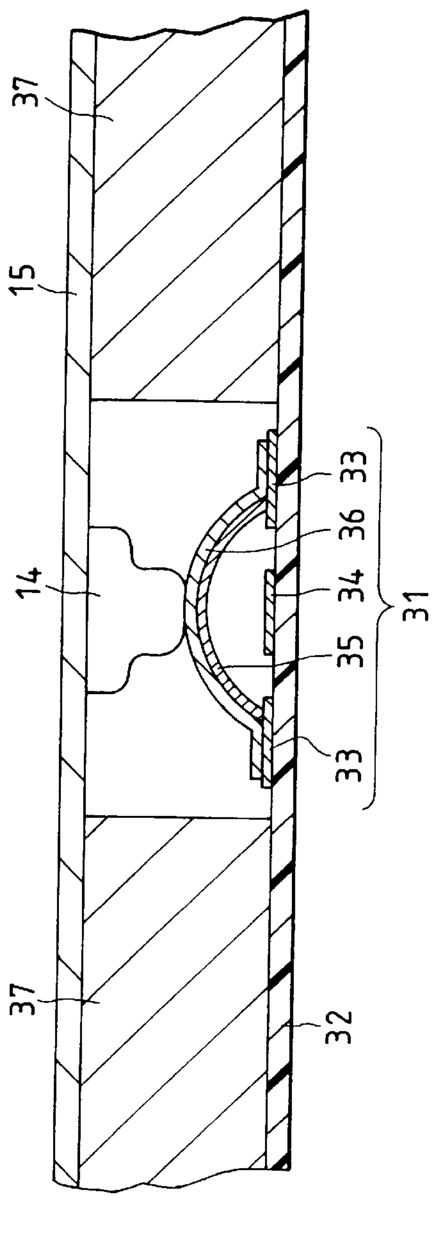
FIG. 12 is a cross-sectional view showing an arrangement of an illuminated switch unit in accordance with a ninth embodiment of the present invention.

As shown in FIG. 12, the ninth embodiment is different from the eighth embodiment in the arrangement of the membrane switch.

More specifically, a membrane switch 31 of this embodiment comprises a horseshoe-like stationary contact 33 which is a conductive pattern formed on a lower insulating substrate 32, a circular stationary contact 34 provided closely inside the horseshoe-like stationary contact 33, a saucer-like diaphragm 35 which is made of a metallic member having sufficient resilience such as phosphor spring or stainless steel, and an adhesive tape 36 which is a resin film having a surface applied with adhesive for bonding diaphragm 35 to stationary contact 33. EL lighting element 15 is fixedly provided above this membrane switch 31 through a spacer 37 which is an adhesive sheet made of resin film having a adhesive applied on thickness of approximately 200 μm and having both surfaces.

With this arrangement, it becomes possible to obtain a further crisp and better click feeling in the operation of the switch and realize a thin configuration of the switch, in addition to the effects obtained from the above-described eighth embodiment.

Tenth Embodiment

Hereinafter, a tenth embodiment of the present invention will be explained.

Figure 13:
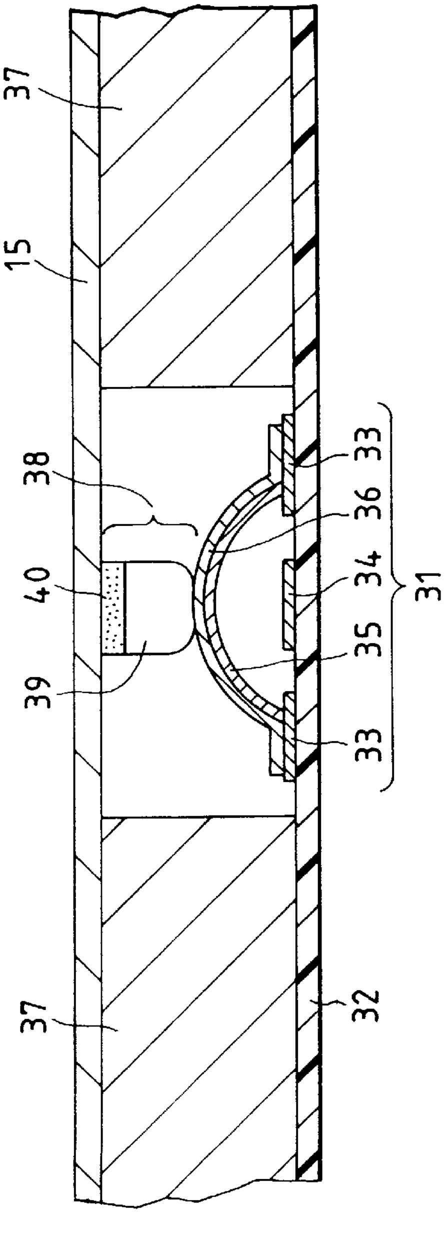
FIG. 13 is a cross-sectional view showing an arrangement of an illuminated switch unit in accordance with a tenth embodiment of the present invention.
Figure 14:
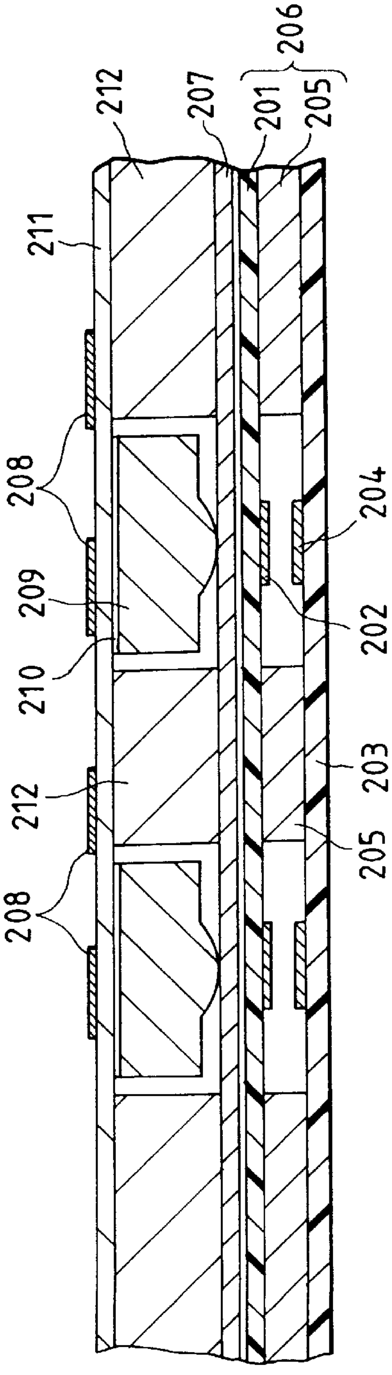
FIG. 14 PRIOR ART
FIG. 14 is a cross-sectional view showing an arrangement of a conventional illuminated switch unit.

As shown in FIG. 13, the tenth embodiment is similar to the seventh to ninth embodiments but different in that a switch operating projection 38 comprises a button 39 fixed on the lower surface of insulating coat layer 28 of EL lighting element 15 by using adhesive 40. Button 39 is formed by punching a high heat-resistant film such as polyether sulfone (PES).

Alternatively, button 39 can be a resin mold product having sufficient rigidity or a metallic sheet, or the like.

With this arrangement, it becomes possible to provide a push switch having a longer projection unattainable by the switch operating projection 14 formed by printing, in addition to the effects of the above-described seventh to ninth embodiments.

As apparent from the foregoing description of the seventh to tenth embodiments, the present invention forms the switch operating projection on the back-surface side of the EL lighting element and disposes this EL lighting element above the push switch. Hence, it becomes possible to remove any obstacles interrupting or intercepting illumination light emitted from the EL lighting element. Hence, uniformity of EL lighting element illumination can be surely obtained. Furthermore, the construction of the illuminated switch unit becomes so simple that a large number of parts and assembling processes can be eliminated. Accordingly, it becomes possible to provide a cheaper illuminated switch unit, bringing great utilities and merits in various industries.

As this invention may be embodied in several forms without departing from the spirit of essential characteristics thereof, the present embodiments described are therefore intended to be only illustrative and not restrictive, since the scope of the invention is defined by the appended claims rather than by the description preceding them, and all changes that fall within metes and bounds of the claims, or equivalents of such metes and bounds, are therefore intended to be embraced by the claims.

What is claimed is:

1. An illuminated switch unit comprising:

a push switch having a movable contact and a stationary contact disposed in a confronting relationship with a predetermined gap; and an electroluminescent lighting element provided above said push switch, said electroluminescent lighting element having a reverse surface provided with a push-switch operating projection for depressing said movable contact to turn on said push switch, said push-switch operating projection being formed by printing insulating resin.

2. The illuminated switch unit in accordance with claim 1, wherein said electroluminescent lighting element is a diffusion-type electroluminescent lighting element.

3. The illuminated switch unit in accordance with claim 1, wherein a surface of said electroluminescent lighting element, serving as a light-emitting surface, is provided with printed indicia.

4. The illuminated switch unit in accordance with claim 1, wherein said push switch is a membrane switch with or without click motion.

5. The illuminated switch unit in accordance with claim 1, wherein said push switch is a push switch with click motion, and said movable contact is a metallic thin plate configured in a diaphragm shape.

6. An illuminated switch unit comprising:

a push switch having a movable contact and a stationary contact disposed in a confronting relationship with a predetermined gap; and an electroluminescent lighting element provided above said push switch, said electroluminescent lighting element having a reverse surface provided with a push-switch operating projection for depressing said movable contact to turn on said push switch, said push-switch operating projection being formed by bonding a rigid member to said reverse surface.

7. The illuminated switch unit in accordance with claim 6, wherein said electroluminescent lighting element is a diffusion-type electroluminescent lighting element.

8. The illuminated switch unit in accordance with claim 6, wherein a surface of said electroluminescent lighting element, serving as a light-emitting surface, is provided with printed indicia.

9. The illuminated switch unit in accordance with claim 6, wherein said push switch is a membrane switch with or without click motion.

10. The illuminated switch unit in accordance with claim 6, wherein said push switch is a push switch with click motion, and said movable contact is a metallic thin plate configured in a diaphragm shape.

* * * * *

UNITED STATES PATENT AND TRADEMARK OFFICE

CERTIFICATE OF CORRECTION

PATENT NO. : 5,950,808 
DATED : September 14, 1999
INVENTOR(S) : Koji Tanabe et al.

It is certified that error appears in the above-identified patent and that said Letters Patent is hereby corrected as shown below:

Title page,
In item [30], the priority claim for Japanese application No. 7-178499, dated July 14, 1995, should be deleted.

Signed and Sealed this

Eleventh Day of June, 2002

*Attest:*

JAMES E. ROGAN

*Attesting Officer* *Director of the United States Patent and Trademark Office*